(12) United States Patent
Yoda et al.

(10) Patent No.: US 10,524,753 B2
(45) Date of Patent: Jan. 7, 2020

(54) X-RAY COMPUTED TOMOGRAPHY APPARATUS AND IMAGE PROCESSING APPARATUS

(71) Applicant: Toshiba Medical Systems Corporation, Otawara-shi (JP)

(72) Inventors: Takahiro Yoda, Nasushiobara (JP); Katsuhito Morino, Utsunomiya (JP); Yasunobu Yamada, Nasushiobara (JP); Yojiro Suzuki, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 657 days.

(21) Appl. No.: 14/961,007

(22) Filed: Dec. 7, 2015

(65) Prior Publication Data

US 2016/0081646 A1    Mar. 24, 2016

Related U.S. Application Data

(63) Continuation of application No. PCT/JP2014/065457, filed on Jun. 11, 2014.

(30) Foreign Application Priority Data

Jun. 12, 2013    (JP) ................................ 2013-123664

(51) Int. Cl.
    *A61B 6/00*    (2006.01)
    *G06T 11/00*    (2006.01)

(52) U.S. Cl.
    CPC ............ *A61B 6/5205* (2013.01); *A61B 6/463* (2013.01); *A61B 6/465* (2013.01); *G06T 11/005* (2013.01); *G06T 2207/10081* (2013.01)

(58) Field of Classification Search
    CPC .. A61B 6/00; A61B 6/46; A61B 6/461; A61B 6/463; A61B 6/465; A61B 6/467; A61B 6/468; A61B 6/52; A61B 6/5205; A61B 6/5211; A61B 6/5294; A61B 2576/00; G06T 1/00; G06T 1/20; G06T 1/60; G06T 7/00; G06T 7/0012; G06T 7/136; G06T 11/00; G06T 11/003; G06T 11/005; G06T 2200/00; G06T 2200/24;

(Continued)

(56) References Cited

U.S. PATENT DOCUMENTS

2004/0086076 A1*    5/2004    Nagaoka ................ A61B 6/032
                                                                378/4
2007/0019851 A1*    1/2007    Nishide ................ G06T 11/005
                                                                382/131

(Continued)

FOREIGN PATENT DOCUMENTS

JP           8-215189        8/1996
JP           9-299360        11/1997

(Continued)

OTHER PUBLICATIONS

International Search Report dated Jul. 8, 2014 in PCT/JP2014/065457, filed Jun. 11, 2014 (with English Translation).

*Primary Examiner* — Anastasia Midkiff
(74) *Attorney, Agent, or Firm* — Oblon, McClelland, Maier & Neustadt, L.L.P.

(57) ABSTRACT

The disclosure relates to an X-ray computed tomography apparatus that includes an X-ray tube, an X-ray detector, preprocessing circuitry, a reconstruction processor, and control circuitry. The X-ray detector is configured to detect X-rays generated from the X-ray tube. The preprocessing circuitry is configured to generate projection data by executing preprocessing for data acquired by the X-ray detector based on a preprocessing condition. The reconstruction processor is configured to generate image data by executing reconstruction processing for the projection data based on a reconstruction condition. The control circuitry is configured to cause a storage to store the projection data in association with the preprocessing condition, and to read out the projection data based on a designated preprocessing condition.

13 Claims, 12 Drawing Sheets

(58) Field of Classification Search
CPC .............. G06T 2200/28; G06T 2210/00; G06T 2210/32; G06T 2210/36; G06T 2210/41; G06T 2211/00; G06T 2211/40; G06T 2211/412; G06T 2211/424; G06T 2207/00; G06T 2207/10; G06T 2207/10072; G06T 2207/10081; G06T 2207/10116; G06T 2207/20; G06T 2207/20004; G06T 2207/20212; G06T 2207/20228
See application file for complete search history.

(56) References Cited

U.S. PATENT DOCUMENTS

| | | | | |
|---|---|---|---|---|
| 2007/0165930 | A1* | 7/2007 | Feuerlein | G06T 1/60 382/128 |
| 2009/0245459 | A1* | 10/2009 | Goto | A61B 6/032 378/16 |
| 2013/0094739 | A1* | 4/2013 | Okabe | A61B 6/032 382/131 |
| 2014/0286559 | A1* | 9/2014 | Mukumoto | A61B 6/545 382/131 |
| 2014/0334708 | A1* | 11/2014 | Sakata | A61B 6/5288 382/131 |

FOREIGN PATENT DOCUMENTS

| | | |
|---|---|---|
| JP | 2003-135451 | 5/2003 |
| JP | 2006-110071 | 4/2006 |
| JP | 2009-50383 | 3/2009 |
| JP | 2010-17597 | 1/2010 |
| JP | 2011-78527 | 4/2011 |

* cited by examiner

| Patient information | Pure raw data | Second projection data | Display image data | Primary preprocessing condition | Secondary preprocessing condition | Reconstruction condition | Image processing condition |
|---|---|---|---|---|---|---|---|
| 1 | D-11 | D-12 | D-13 | AA | BA | CA | DA |
| 2 | D-21 | D-22 | D-23 | AB | BB | CB | DB |
| 3 | D-31 | D-32 | D-33 | AC | BC | CC | DC |
| 4 | D-41 | D-42 | D-43 | AD | BD | CD | DD |
| ⋮ | ⋮ | ⋮ | ⋮ | ⋮ | ⋮ | ⋮ | ⋮ |
| 20 | D-201 | D-202 | D-203 | AY | BH | CG | DG |

FIG. 4

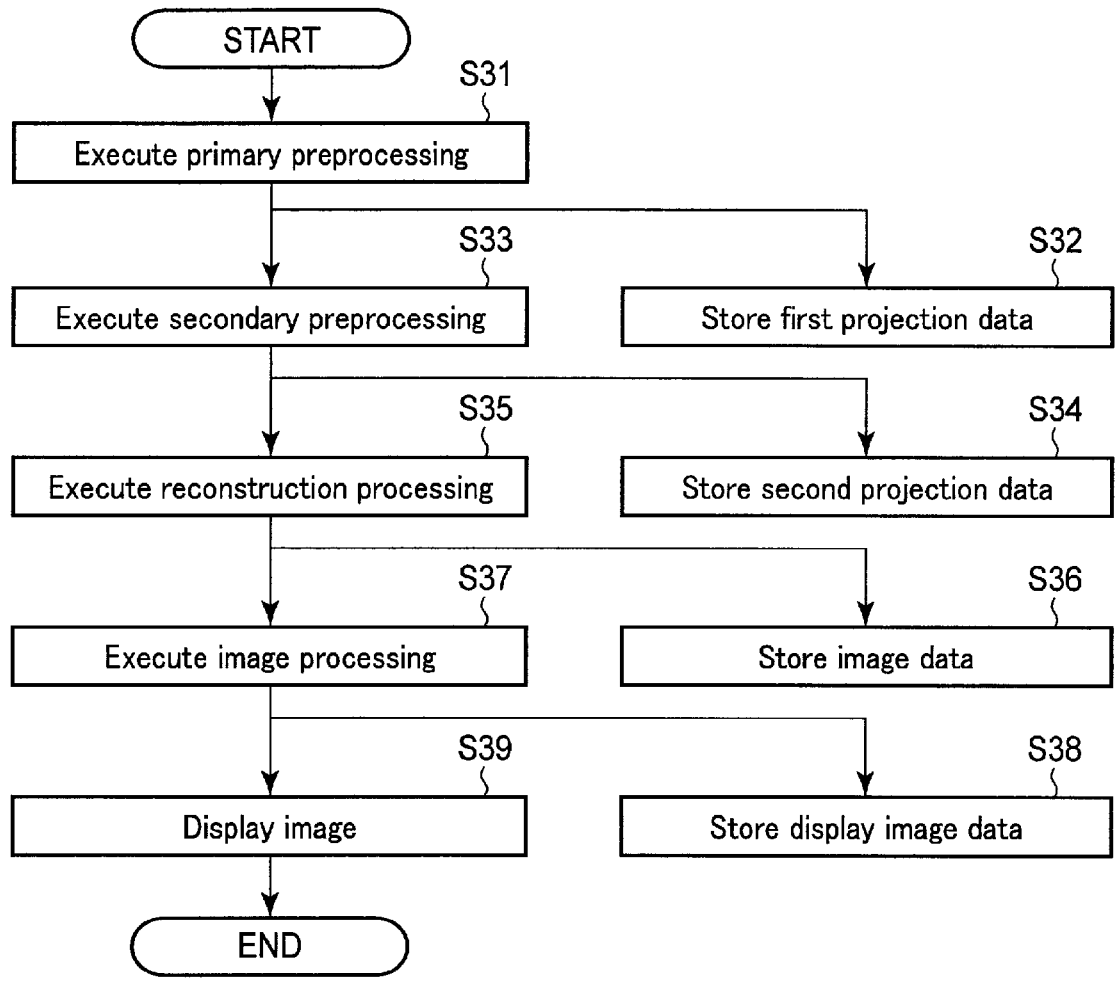
F I G. 6

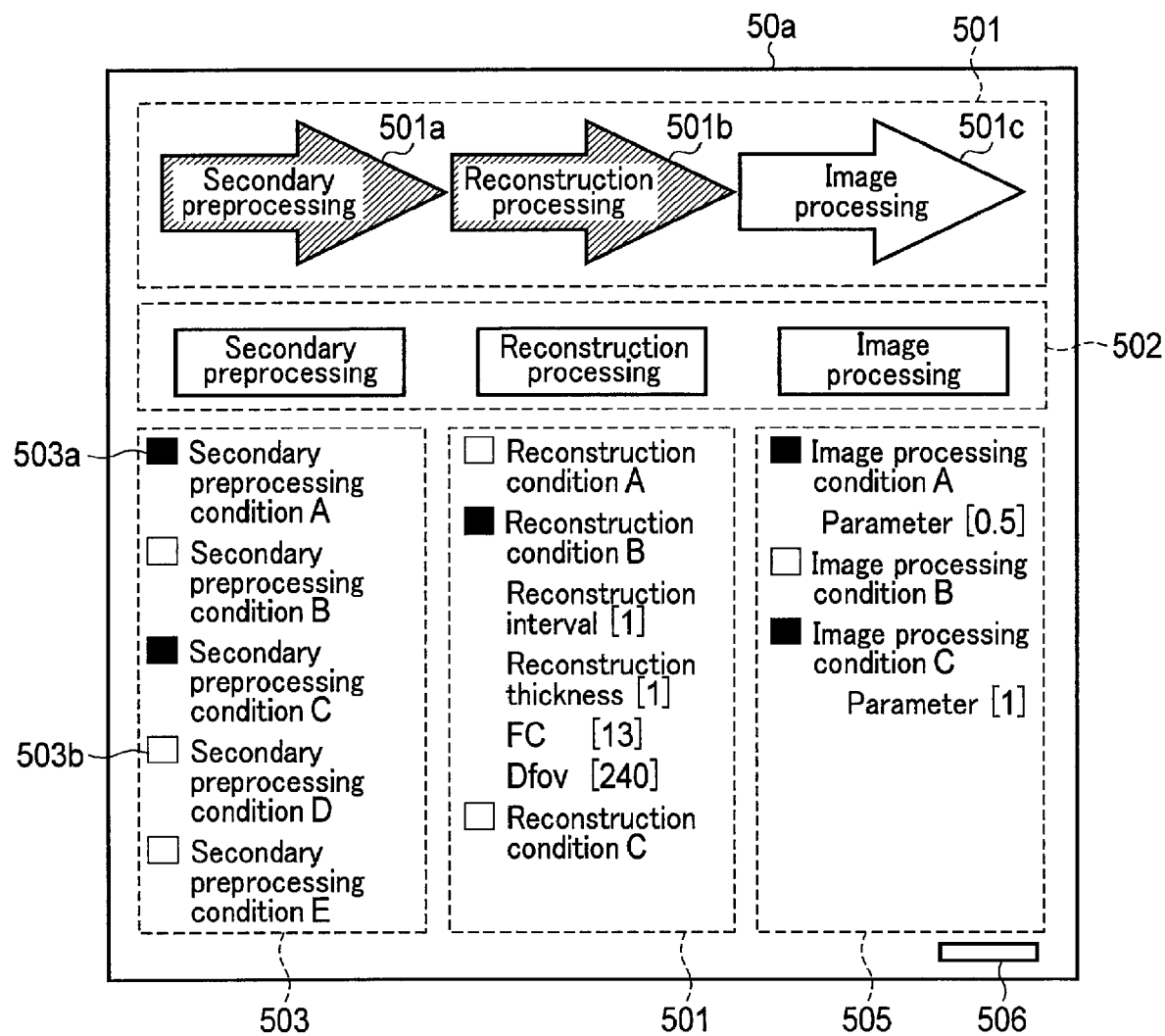
F I G. 7A

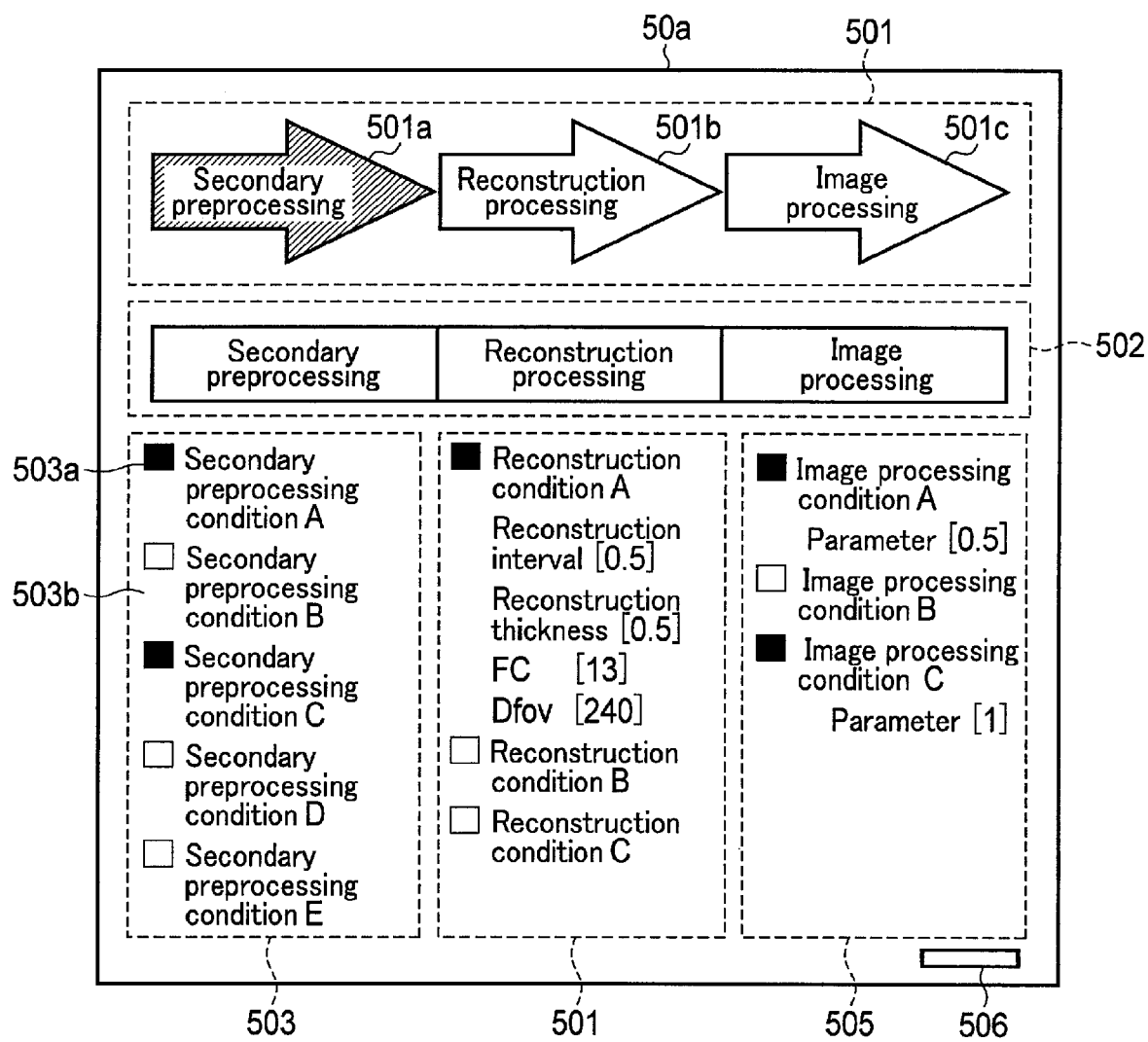
F I G. 7B

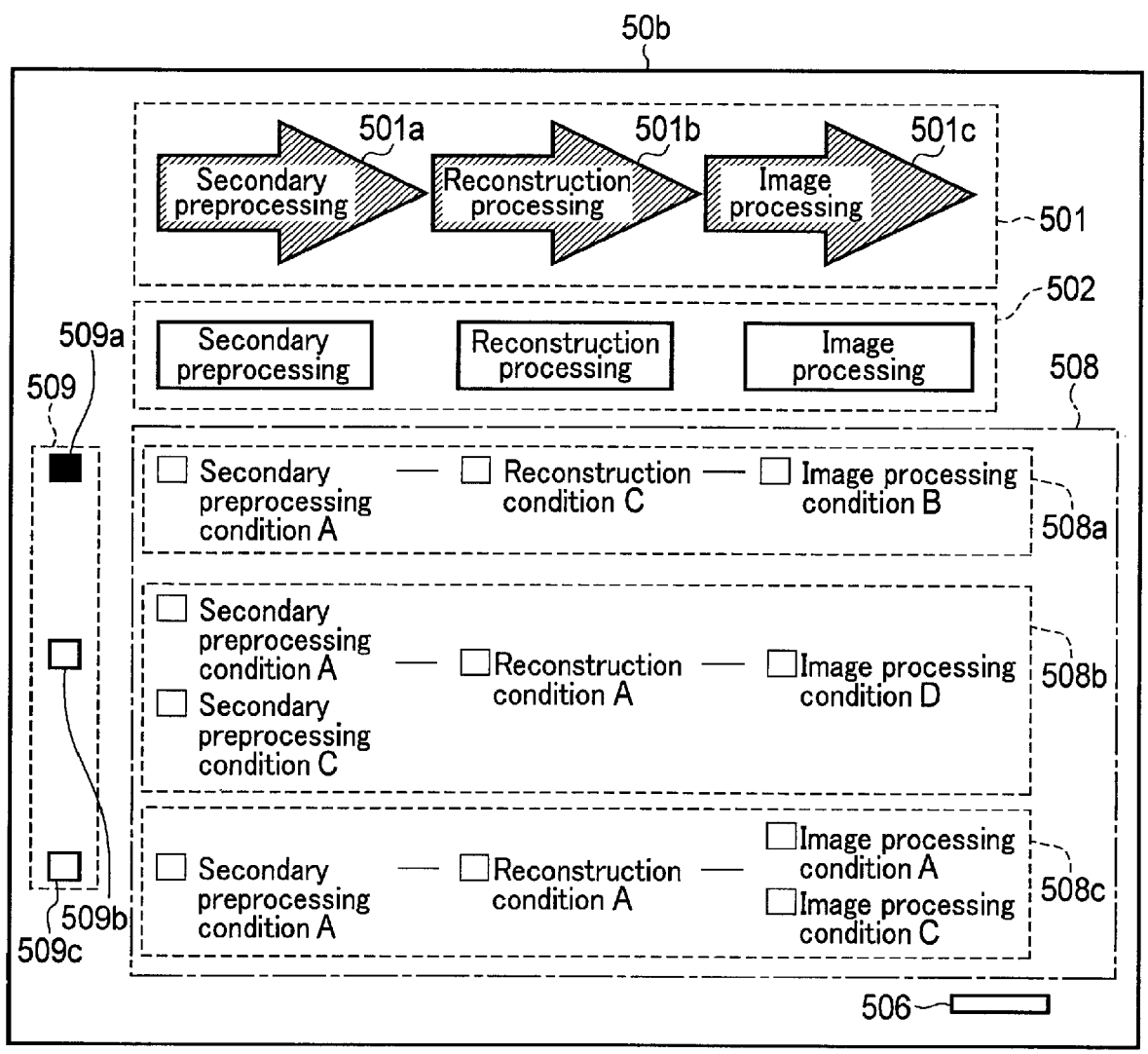
F I G. 8A

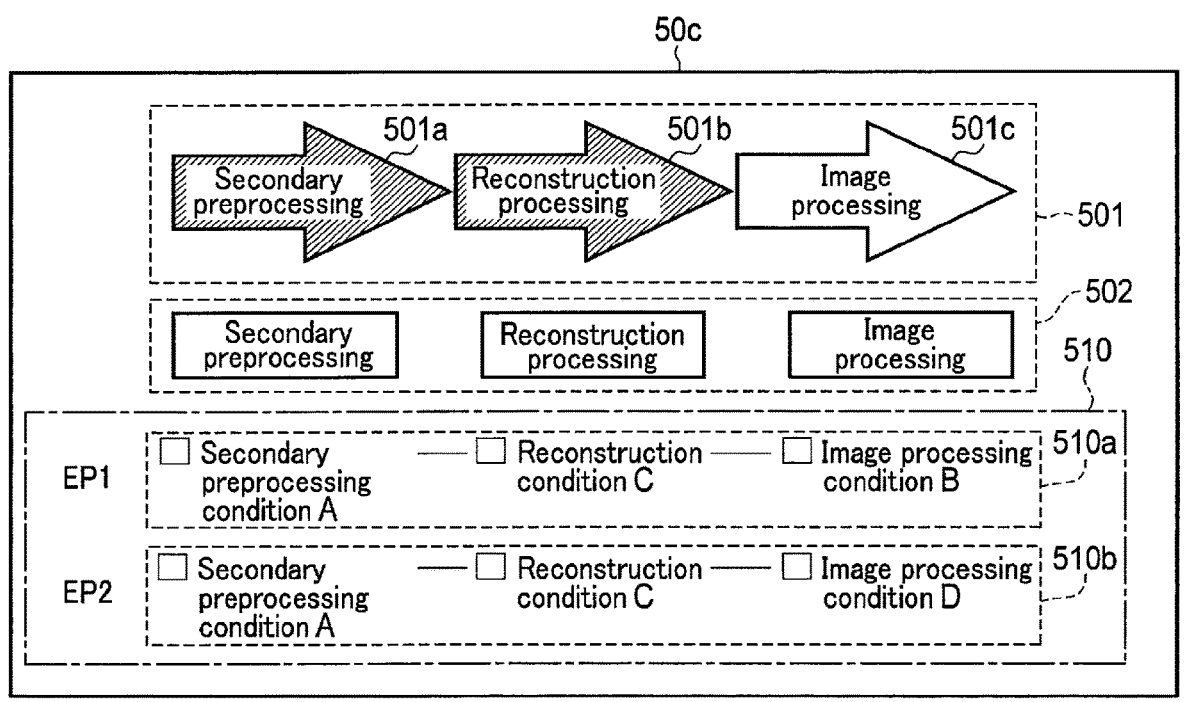
F I G. 9B

X-RAY COMPUTED TOMOGRAPHY APPARATUS AND IMAGE PROCESSING APPARATUS

CROSS-REFERENCE TO RELATED APPLICATIONS

This application is a Continuation Application of PCT application No. PCT/JP2014/065457, filed on Jun. 11, 2014, and is based upon and claims the benefit of priority from Japanese Patent Application No. 2013-123664, filed on Jun. 12, 2013, the entire contents of which are incorporated herein by reference.

FIELD

Embodiments described herein relate generally to an X-ray computed tomography apparatus and an image processing apparatus.

BACKGROUND

An X-ray CT (Computed Tomography) apparatus is an apparatus which provides the medical information of an object to the user in an image form. This apparatus plays an important role in medical activities such as diagnosis and medical treatment by doctors and the like. When an X-ray CT apparatus starts imaging an object, the X-ray detector detects X-rays emitted from the X-ray tube and transmitted through the object. A DAS (Data Acquisition System) converts a signal output from the X-ray detector into a voltage signal for each channel, amplifies the signal, and converts it into a digital signal, thereby generating pure raw data. Projection data is generated by executing preprocessing for the pure raw data. A storage device stores the projection data together with, for example, supplementary information such as an imaging position and an imaging angle. CT reconstruction processing is executed according to the procedure shown in FIG. 10 in accordance with a display image acquisition request from the user. In CT reconstruction processing, first of all, the user reads out projection data from the storage device in accordance with the image display acquisition request from the user (step S1). The data processing apparatus of the X-ray CT apparatus then executes reconstruction processing for the projection data (step S2). Image processing is executed for the data of the reconstructed image after the reconstruction processing (step S3). Finally, a display device displays the display image data corresponding to the acquisition request from the user (step S4). Conventionally, the procedure for CT reconstruction processing like that shown in FIG. 10 is a fixed procedure, in which intermediate data processed midway through the processing is only temporarily stored in a memory and discarded upon completion of the CT reconstruction processing.

For this reason, even when executing CT reconstruction processing with several data processing conditions, e.g., reconstruction processing conditions, common to CT reconstruction processing executed in the past, the X-ray CT apparatus reads out projection data from the storage device, and executes reconstruction processing and image processing for the projection data. For this reason, even when executing CT reconstruction processing with several data processing conditions common to CT reconstruction processing executed in the past, the X-ray CT apparatus requires almost the same time as that for regular CT reconstruction processing. This makes it difficult to increase the time for diagnosis, medical treatment, and the like.

BRIEF DESCRIPTION OF THE DRAWINGS

FIG. 4 is a third view for explaining the storage form of data concerning the object in the storage unit of the X-ray computed tomography apparatus according to this embodiment.

FIG. 6 is a flowchart concerning write processing by the X-ray computed tomography apparatus according to this embodiment.

FIG. 7A is a view showing a change in the display form of part of a CT reconstruction processing setting screen as the first example in accordance with the first example of CT reconstruction conditions selected by the user.

FIG. 7B is a view showing a change in the display form of part of the CT reconstruction processing setting screen as the first example in accordance with the second example of CT reconstruction conditions selected by the user.

FIG. 8A is a view showing a change in the display form of part of a CT reconstruction processing setting screen as the second example in accordance with the first example of CT reconstruction conditions selected by the user.

FIG. 9B is a view showing a change in the display form of part of the expert plan editing screen in accordance with the second example of CT reconstruction conditions input by the user.

DETAILED DESCRIPTION

Figure 1:
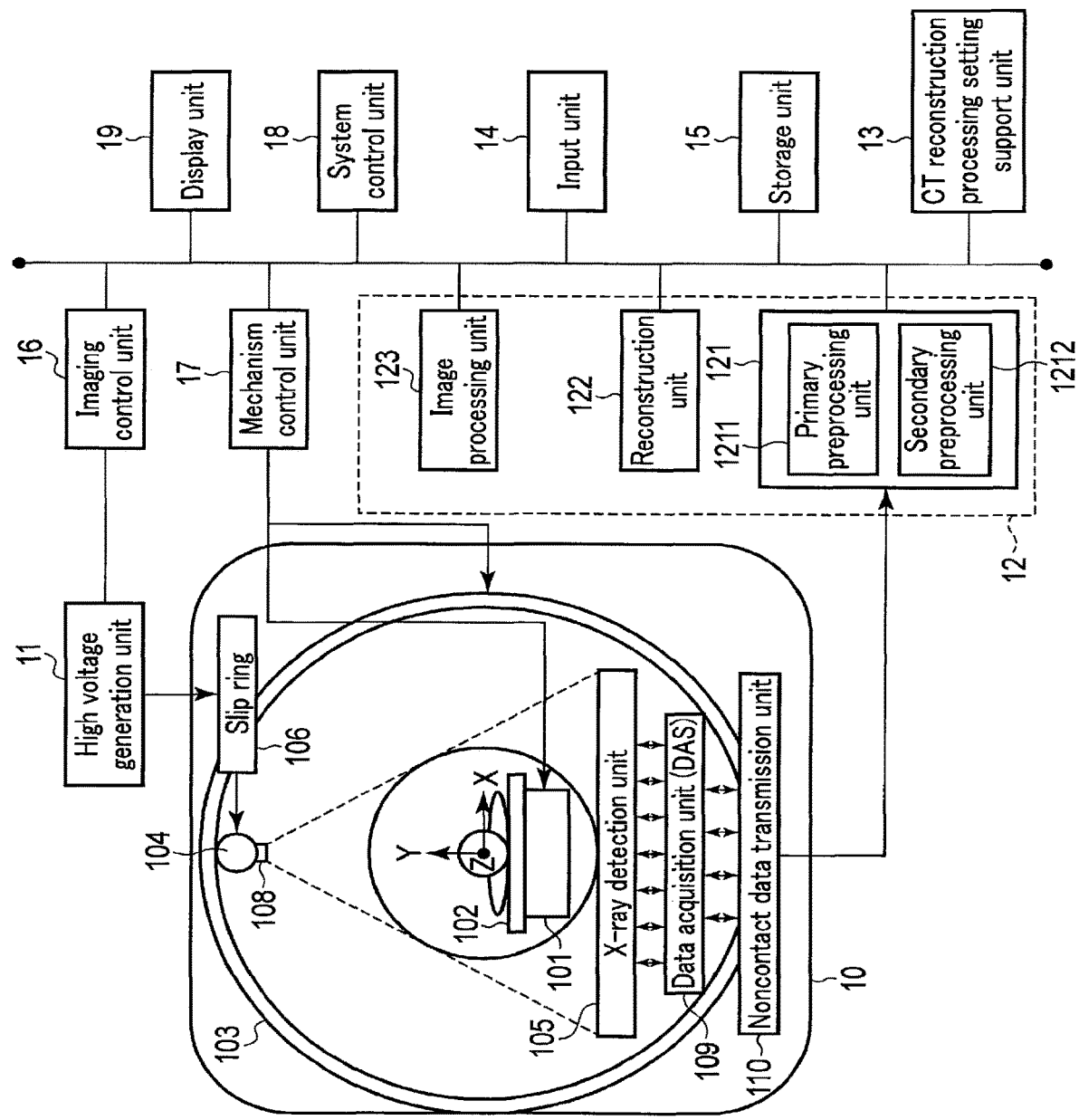
FIG. 1 is a block diagram showing the arrangement of an X-ray computed tomography apparatus according to an embodiment.

In general, according to one embodiment, an X-ray computed tomography apparatus includes an X-ray tube, an X-ray detector, preprocessing circuitry, a reconstruction processor and control circuitry. The X-ray tube configured to generate X-rays. The X-ray detector configured to detect X-rays generated from the X-ray tube and transmitted through an object. The preprocessing circuitry configured to generate projection data by executing preprocessing for data acquired by the X-ray detector, based on a preprocessing condition. The reconstruction processor configured to generate image data by executing reconstruction processing for the projection data based on a reconstruction condition. The control circuitry configured to cause a storage to store the projection data in association with the preprocessing condition and read out, based on a designated preprocessing condition, corresponding projection data from the storage.

An X-ray computed tomography apparatus according to an embodiment will be described below with reference to the accompanying drawings. Note that the same reference numerals in the following description denote constituent elements having almost the same functions and arrangements, and a repetitive description will be made only when required.

FIG. 1 is a block diagram showing the arrangement of an X-ray computed tomography apparatus according to this embodiment. The X-ray computed tomography apparatus according to this embodiment (to be referred to as this X-ray computed tomography apparatus hereinafter) includes a CT gantry 10, a high voltage generation unit 11, a data processing unit 12, a CT reconstruction processing setting support unit 13, an input unit 14, a storage unit 15, an imaging control unit 16, a mechanism control unit 17, a system control unit 18, and a display unit 19.

The CT gantry 10 includes a bed 101, a top 102, a rotating support mechanism 103, an X-ray tube 104, an X-ray detection unit 105, a slip ring 106, an X-ray collimator 108, a data acquisition unit 109, and a noncontact data transmission unit 110.

The bed 101 movably supports the top 102 on which an object is placed. Driving a bed driving unit (not shown) under the control of the mechanism control unit 17 (to be described later) will move the top 102 in a direction along the Z-axis. As the top 102 moves, the object is moved into an opening for diagnosis (not shown).

The rotating support mechanism 103 is accommodated in the CT gantry 10. The rotating support mechanism 103 includes a rotating ring and a ring support mechanism which supports the rotating ring so as to make it rotatable about a rotation axis Z. The X-ray tube 104 and the X-ray detection unit 105 are mounted on the rotating ring. As a rotation driving unit (not shown) is driven under the control of the mechanism control unit 17 (to be described later), the rotating ring is rotated about the rotation axis Z.

The X-ray tube 104 emits X-rays from the focus upon receiving a tube voltage applied and a tube current supplied from the high voltage generation unit 11 via the slip ring 106. The high voltage generation unit 11 generates a high voltage for applying a tube voltage between the electrodes of the X-ray tube 104 and a tube current to be supplied to the X-ray tube 104 under the control of the imaging control unit 16 (to be described later). The X-ray collimator 108 is attached to the X-ray radiation window of the X-ray tube 104. The X-ray collimator 108 has a plurality of aperture blades to reduce unnecessary exposure on an object. The plurality of aperture blades are moved under the control of the mechanism control unit 17 (to be described later). Moving the plurality of aperture blades will form cone-beam X-rays having an X-ray spread angle (fan angle) within the X and Y planes perpendicular to the rotation axis Z and an X-ray spread angle (cone angle) in the rotation axis Z direction.

The X-ray detection unit 105 is mounted at a position and angle at which it faces the X-ray tube 104 through the rotation axis Z. The X-ray detection unit 105 includes a plurality of X-ray detection elements. The plurality of X-ray detection elements detect X-rays transmitted through an object and output current signals corresponding to the intensities of X-rays to the data acquisition unit 109. Assume that in the following description, a single X-ray detection element forms a single channel. A plurality of channels are two-dimensionally arrayed in two directions including a direction (slice direction) parallel to the rotation axis Z and an arc direction (channel direction) which is perpendicular to the rotation axis Z and gradually curves around the X-ray focus. An X-ray detector having such a two-dimensional detection element array may be formed by arranging a plurality of arrays, each having detection elements arrayed in a line in the channel direction, in the slice direction, or by arraying a plurality of modules formed by arraying detection elements in an M×N matrix.

The data acquisition unit 109 (data acquisition system) converts a current signal into digital data (to be referred to as pure raw data hereinafter) via each channel of the X-ray detection unit 105. For this purpose, the data acquisition unit 109 is provided with, for each channel, for example, an I-V converter which converts a current signal into a voltage signal, an integrator which periodically integrates such voltage signals in synchronism with an X-ray irradiation period, an amplifier which amplifies an output signal from the integrator, and an analog/digital converter which converts the output signal from the amplifier into a digital signal. Pure raw data is transmitted to a preprocessing unit 121 via the noncontact data transmission unit 110 using magnetic transmission/reception or optical transmission/reception. The storage unit 15 stores the pure data in association with data representing a channel number, a detection element array number, and a view angle at the time of data acquisition.

The data processing unit 12 generates display image data by executing a plurality of image processes respectively corresponding to a plurality of processing sequences for pure raw data acquired by the data acquisition unit 109. A series of these processes performed by the data processing unit 12 will be referred to as CT reconstruction processing. CT reconstruction processing performed by this X-ray computed tomography apparatus will be described in detail later. The data processing unit 12 includes the preprocessing unit 121, a reconstruction unit 122, and an image processing unit 123.

The preprocessing unit 121 generates projection data by executing preprocessing for pure raw data in accordance with preprocessing conditions designated by the user. The generated projection data is output to the reconstruction unit 122 (to be described later). The projection data is the integral value of X-ray absorption coefficients concerning the respective detection elements of the X-ray detection unit 105. Preprocessing is divided into processing (to be referred to as primary preprocessing hereinafter) basically necessary for the generation of projection data from pure raw data and correction processing (to be referred to as secondary preprocessing hereinafter) for correcting undesired characteristics of hardware of this X-ray computed tomography apparatus. Primary preprocessing is, for example, logarithmic conversion processing. Secondary preprocessing is, for example, spatial filter processing. The preprocessing unit 121 includes a primary preprocessing unit 1211 and a secondary preprocessing unit 1212.

The primary preprocessing unit 1211 generates the first projection data by executing primary preprocessing for pure raw data in accordance with primary processing conditions. Primary processing corresponds to logarithmic conversion processing, X-ray intensity correction, property fluctuation correction for the detection system, radiation quality hardening correction, and the like. Primary preprocessing conditions include the type of preprocessing executed in primary preprocessing and its parameters.

The secondary preprocessing unit 1212 generates the second projection data by executing secondary preprocessing for the first projection data in accordance with secondary preprocessing conditions. Assume that the simple wording "projection data" indicates the second projection data. Secondary preprocessing corresponds to, for example, spatial filter processing, body movement correction, and scattered X-ray correction. Secondary preprocessing conditions include the type of preprocessing executed in secondary preprocessing and its parameters.

Note that the user can change preprocessing to be executed as primary preprocessing and preprocessing to be executed as secondary preprocessing among a plurality of types of preprocessing, as needed, via the input unit 14. For example, when the user basically needs to perform a specific type of preprocessing of a plurality of types of preprocessing, the specific type of preprocessing is assigned to primary preprocessing.

The reconstruction unit 122 generates image data (also called 3D image data or volume data) by executing reconstruction processing for projection data in accordance with reconstruction conditions designated by the user. Reconstruction conditions include reconstruction methods and reconstruction parameters. The reconstruction methods include the Feldkamp method and a sequential approximate reconstruction method. The reconstruction parameters include a reconstruction function and a slice thickness (reconstruction interval).

The image processing unit 123 generates display image data by executing image processing for image data in accordance with image processing conditions designated by the user. The image processing includes projection processing for generating 2D image data for display from 3D image data and image processing for the 2D image data. For example, the projection processing includes rendering processing and slice conversion processing. In addition, the image processing includes tone conversion for operating the contrast of a 2D image. The image processing conditions include the type of image processing and its parameters.

Note that data other than display image data which are generated from pure raw data in the process of CT reconstruction processing will be collectively referred to as intermediate image data. The intermediate image data in this embodiment indicate the first projection data, the second projection data, and image data. Display image data will be referred to as final image data.

The CT reconstruction processing setting support unit 13 provides a setting screen (to be referred to as a CT reconstruction processing setting screen hereinafter) for allowing the user to easily and simply set CT reconstruction conditions. CT reconstruction conditions are a generic term for conditions associated with CT reconstruction processing, such as primary preprocessing conditions, secondary preprocessing conditions, reconstruction conditions, and image processing conditions. The CT reconstruction processing setting screen provided by the image generation condition setting support unit will be described later.

The input unit 14 includes input devices such as a mouse and a keyboard. Note that as input devices, a trackball, a touch panel, switches, and the like may be used. The input unit 14 functions as an interface with which the user inputs instruction information to the X-ray computed tomography apparatus according to this embodiment. The instruction information includes, for example, imaging conditions, CT reconstruction conditions, and storage conditions.

Imaging conditions include an imaging method and scan conditions, and are input in accordance with user operation on an imaging condition setting screen displayed by the display unit 19 (to be described later). The imaging method is, for example, scanography, helical imaging, or conventional scan imaging. The user can select an imaging method to be used from these imaging methods via the input unit 14. The scan conditions include a tube voltage, a tube current, a scan velocity, an imaging time, a helical pitch, an imaging slice thickness, an irradiation range, and an irradiation position, when performing, for example, helical scan imaging, and are input by the user via the input unit 14.

CT reconstruction conditions are input in accordance with user operation on a setting screen provided by the CT reconstruction processing setting support unit 13. Input items include, for example, primary preprocessing conditions, secondary preprocessing conditions, reconstruction conditions, and image processing conditions.

Storage conditions are conditions for designating data, of data concerning an object, which are to be stored in the storage unit 15. The data concerning the object represent pure raw data, intermediate image data, and final image data. Storage conditions are input in accordance with user operation on a storage condition setting screen displayed on the display unit 19.

The storage unit 15 is a semiconductor storage device such as a Flash SSD (Solid State Disk), which is a semiconductor storage element, an HDD (Hard Disk Drive), or the like. Under the control of the system control unit 18, the storage unit 15 stores intermediate image data together with CT reconstruction conditions which have been executed for pure raw data to generate the intermediate image data from the pure raw data. In addition, when final image data is designated in storage conditions, under the control of the system control unit 18, the storage unit 15 stores the final image data together with CT reconstruction conditions which have been executed for the pure raw data to generate the final image data. In addition, when pure raw data is designated in storage conditions, under the control of the system control unit 18, the storage unit 15 stores the pure raw data acquired by the data acquisition unit 109.

Figure 2:
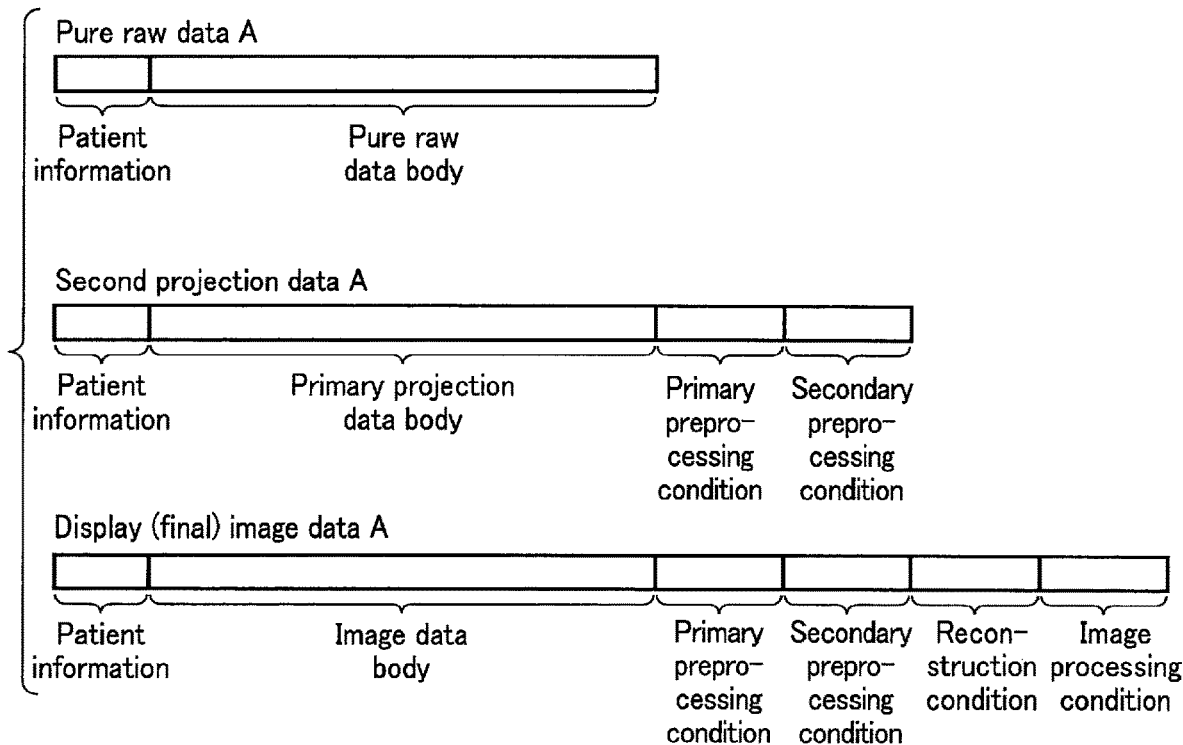
FIG. 2 is a first view for explaining the storage form of data concerning an object in the storage unit of the X-ray computed tomography apparatus according to this embodiment.

FIG. 2 is a first view for explaining the storage form of data concerning an object in the storage unit 15 of the X-ray computed tomography apparatus according to this embodiment. Note that as storage conditions, pure raw data, the second projection data, and display image data have been designated. The storage unit 15 stores intermediate image data and final image data in association with executed CT reconstruction conditions and patient information. The data stored in the storage unit 15, which are described with reference to FIG. 2, are constituted by patient information, CT reconstruction conditions, and a data body. For example, as shown in FIG. 2, the storage unit 15 stores pure raw data A acquired by the data acquisition unit 109 together with patient information under the control of the system control unit 18. In addition, the storage unit 15 stores second projection data A generated by the secondary preprocessing unit 1212, together with patient information, primary preprocessing conditions, and secondary preprocessing conditions, under the control of the system control unit 18. The storage unit 15 also stores display (final) image data A generated by the image processing unit 123, together with patient information, primary preprocessing conditions, secondary preprocessing conditions, reconstruction condition, and image processing conditions, under the control of the system control unit 18.

Note that since intermediate image data and final image data are both generated from pure raw data, the arrangement of data stored in the storage unit 15 is not limited to that shown in FIG. 2 as long as the intermediate image data and the final image data are associated with the pure raw data together with CT reconstruction conditions which have been executed for the pure raw data. Another arrangement will be described below with reference to FIG. 3.

Figure 3:
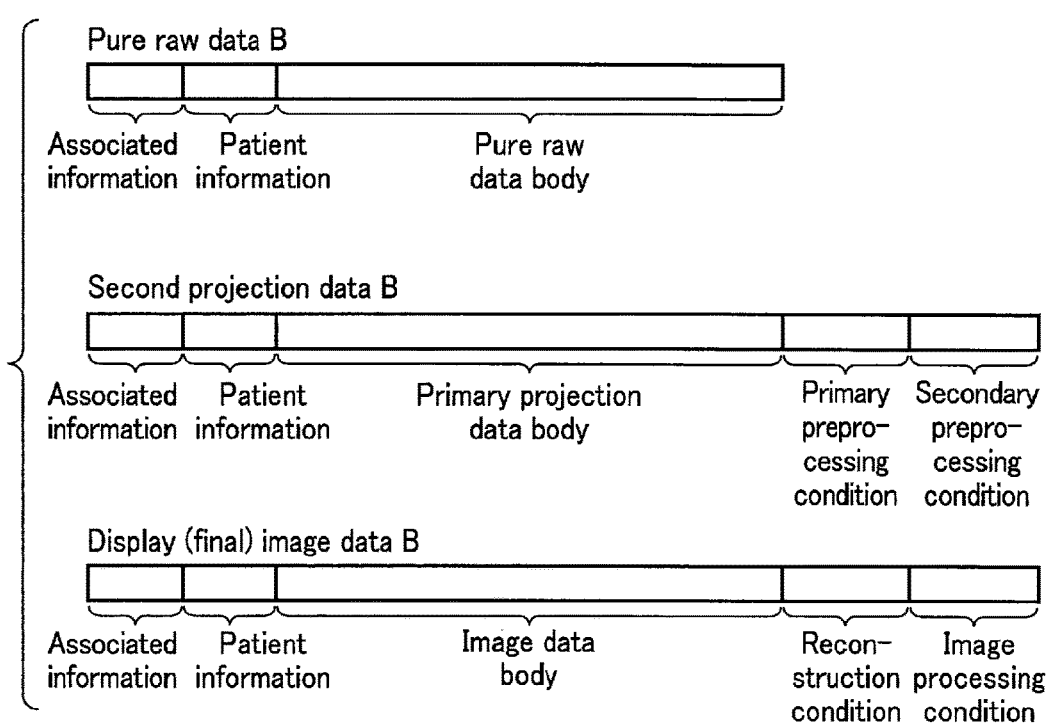
FIG. 3 is a second view for explaining the storage form of data concerning the object in the storage unit of the X-ray computed tomography apparatus according to this embodiment.

FIG. 3 is a second view for explaining the storage form of data concerning an object in the storage unit 15 of the X-ray computed tomography apparatus according to this embodiment. Assume that pure raw data, second projection data, and display image data are designated as storage conditions. The data stored in the storage unit 15, which will be described with reference to FIG. 3, is constituted by associated information, patient information, CT reconstruction conditions, and a data body. For example, as shown in FIG. 3, the storage unit 15 stores pure raw data B acquired by the data acquisition unit 109 together with associated information and patient information, under the control of the system control unit 18. In addition, the storage unit 15 stores second projection data B generated by the secondary preprocessing unit 1212 based on pure raw data B, together with associated information, patient information, primary preprocessing conditions, and secondary preprocessing conditions, under the control of the system control unit 18. The storage unit 15 also stores display (final) image data B generated by the image processing unit 123 based on second projection data B, together with associated information, patient information, reconstruction conditions, and image processing conditions.

Primary preprocessing conditions and secondary preprocessing conditions are not associated with display (final) image data B. However, since display (final) image data B and second projection data B are associated with each other by associated information, display (final) image data B is also associated with primary preprocessing conditions and secondary preprocessing conditions. Therefore, CT reconstruction conditions associated with display (final) image data B may only be CT reconstruction conditions which have been executed for second projection data B. This makes it possible to store intermediate image data and final image data generated from the same pure raw data while associating them with each other by associated information. Therefore, the data structure described with reference to FIG. 3 can facilitate management in the storage unit 15 more than the data structure described with reference to FIG. 2.

FIG. 4 is a third view for explaining the storage form of data concerning an object in the storage unit 15 of the X-ray computed tomography apparatus according to this embodiment. Assume that pure raw data, second projection data, and display image data are designated as storage conditions.

The storage unit 15 may individually store pure raw data, second projection data, display image data, primary preprocessing conditions, secondary preprocessing conditions, reconstruction conditions, and image processing conditions, and manage them while associating them with each other using a data management table like that shown in FIG. 4. For example, this table indicates that referring to patient information "1", pure raw data, second projection data, and display image data are respectively stored at storage positions corresponding to the address "D-11", the address "D-12", and the address "D-13". In addition, the primary preprocessing condition "AA", the secondary preprocessing condition "BA", the reconstruction condition "CA", and the image processing condition "DA" are associated with the patient information "1".

The imaging control unit 16 outputs control signals corresponding to scan conditions input by the user via the input unit 14, e.g., a tube voltage, a tube current, a scan velocity, and an imaging time, to the high voltage generation unit 11 and the X-ray detection unit 105.

The mechanism control unit 17 outputs control signals corresponding to scan conditions input by the user via the input unit 14, e.g., a scan velocity, an imaging time, a helical pitch, and an imaging slice thickness, to the rotation driving unit and the bed driving unit. In addition, the mechanism control unit 17 controls the X-ray collimator 108 based on an irradiation range and an irradiation position which are input by the user via the input unit 14. More specifically, the mechanism control unit 17 outputs control signals for respectively moving a plurality of aperture blades of the X-ray collimator 108 to the X-ray collimator 108 so as to irradiate an irradiation range and an irradiation position input by the user with X-rays emitted from the X-ray tube 104.

The system control unit 18 includes a CPU (Central Processing Unit) and memory circuitry. The system control unit 18 temporarily stores information input to the X-ray computed tomography apparatus according to this embodiment in the memory circuitry via the input unit 14. The system control unit 18 controls each unit of the X-ray computed tomography apparatus according to this embodiment based on the input information. More specifically, the system control unit 18 controls writing and reading of data to and from the storage unit 15.

When writing data to the storage unit 15, the system control unit 18 makes the storage unit 15 store intermediate image data together with CT reconstruction conditions in accordance with storage conditions input by the user via the input unit 14. The CT reconstruction conditions are conditions actually executed to generate pure raw data from the intermediate image data. In addition, the system control unit 18 makes the storage unit 15 store final image data together with the CT reconstruction conditions in accordance with storage conditions input by the user via the input unit 14. The CT reconstruction conditions are conditions actually executed to generate the final image data from pure raw data.

When reading out data from the storage unit 15, the system control unit 18 searches the storage unit 15 to specify data to be read out in accordance with the CT reconstruction conditions input in accordance with user operation on the CT reconstruction processing setting screen. More specifically, the system control unit 18 searches the storage unit 15 in accordance with the CT reconstruction conditions designated by the user to specify the first projection data stored together with primary preprocessing conditions matching those designated by the user. The specified first projection data is then output to the secondary preprocessing unit 1212. In addition, the system control unit 18 searches the storage unit 15 in accordance with the CT reconstruction conditions designated by the user to specify the second projection data stored together with the primary preprocessing conditions and the secondary preprocessing conditions which respectively match those designated by the user. The specified second projection data is then output to the reconstruction unit 122. Furthermore, the system control unit 18 searches the storage unit 15 in accordance with the CT reconstruction conditions designated by the user to specify image data stored together with the primary preprocessing conditions, the secondary preprocessing conditions, and the reconstruction conditions which respectively match those designated by the user. The specified image data is then output to the image processing unit 123. The system control unit 18 also searches the storage unit 15 in accordance with image processing conditions designated by the user to specify display image data stored together with primary preprocessing condition, secondary preprocessing conditions, reconstruction conditions, and image processing conditions respectively matching those designated by the user. The specified display image data is then output to the display unit 19. Note that when there are a plurality of data matching designated CT reconstruction conditions, the system control unit 18 reads out data having undergone the progression of a processing procedure from the storage unit 15. When, for example, image data and second projection data are specified from the storage unit 15 in accordance with CT reconstruction conditions, the system control unit 18 reads out image data having undergone the progression of a processing procedure from the storage unit 15. In addition, assume that the first projection data, the second projection data, image data, and display image data are set as storage conditions, and that there is no first projection data stored together with primary preprocessing conditions matching those designated by the user, when the system control unit 18 searches the storage unit 15 in accordance with CT reconstruction conditions designated by the user. In this case, the system control unit 18 reads out pure raw data from the storage unit 15. Assume that the second projection data and image data are set as storage conditions, and that there is no second projection data stored together with secondary preprocessing conditions matching those designated by the user, when the system control unit 18 searches the storage unit 15 in accordance with CT reconstruction conditions designated by the user. In this case, the system control unit 18 reads out pure raw data from the storage unit 15.

The display unit 19 displays a display image generated by CT reconstruction processing. The display unit 19 also displays a CT reconstruction processing setting screen provided by the CT reconstruction processing setting support unit 13. In addition, the storage unit 15 displays a storage condition setting screen and an imaging condition setting screen.

(Readout Function)

The readout function is a function of making the system control unit 18 of this X-ray computed tomography apparatus search the storage unit 15 in accordance with CT reconstruction conditions input in accordance with user operation on a CT reconstruction processing setting screen provided by the CT reconstruction processing setting support unit 13 to read out one of pure raw data, intermediate image data, and final image data. Data read out from the storage unit 15 by processing related to the readout function (to be referred to as readout processing hereinafter) is output to each unit for CT reconstruction processing. Readout processing will be described below with reference to FIG. 5.

Figure 5:
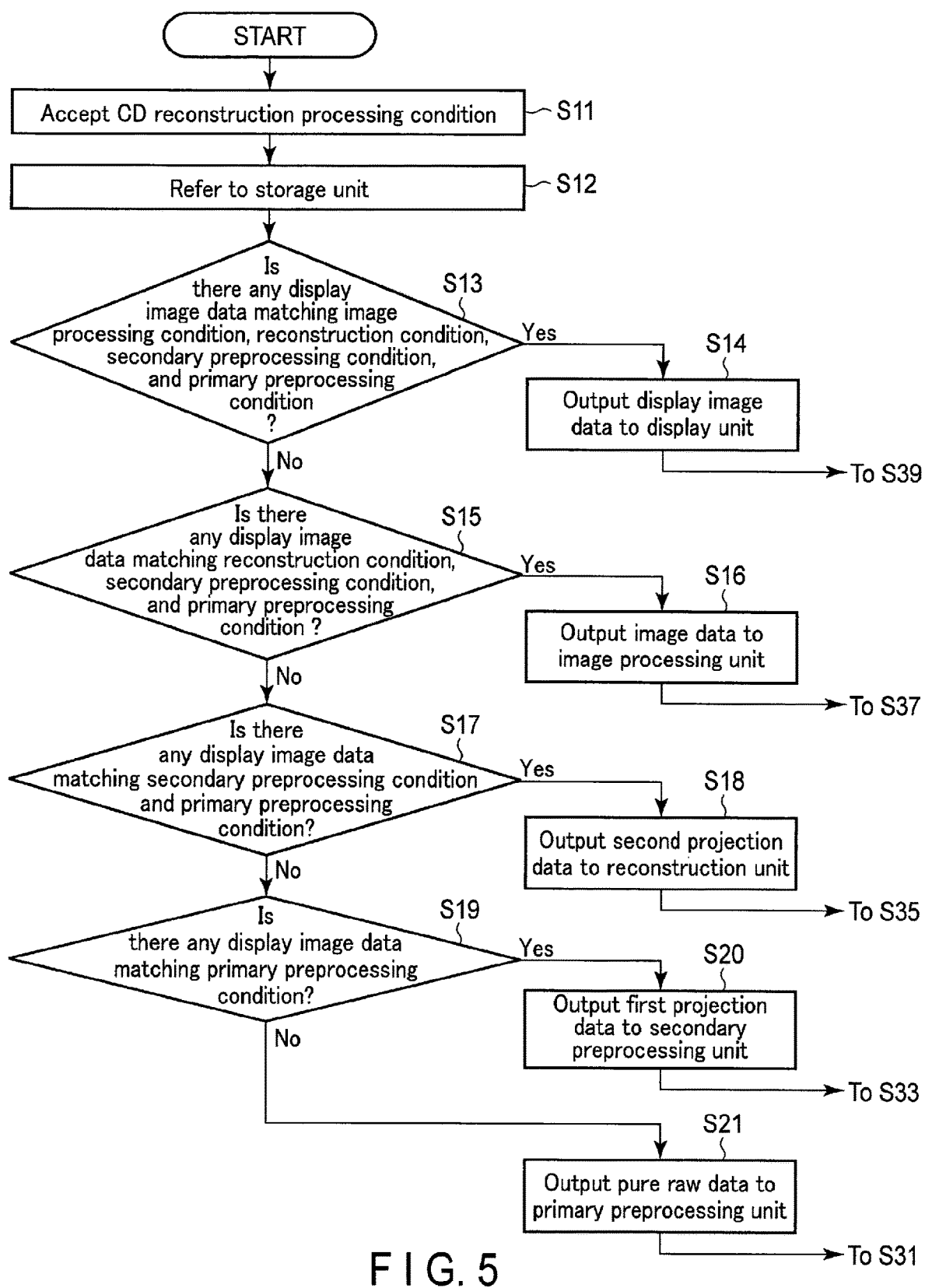
FIG. 5 is a flowchart concerning readout processing by the X-ray computed tomography apparatus according to this embodiment.

FIG. 5 is a flowchart concerning readout processing by the X-ray computed tomography apparatus according to this embodiment.

(Step S11)

The system control unit 18 accepts CT reconstruction conditions input in accordance with user operation on a CT reconstruction processing setting screen. The CT reconstruction conditions include primary preprocessing conditions, secondary preprocessing conditions, reconstruction conditions, and image processing conditions.

(Step S12)

The system control unit 18 searches the storage unit 15 in accordance with the CT reconstruction conditions designated by the user in step S11.

(Step S13)

If the storage unit 15 stores display image data stored together with primary preprocessing conditions, secondary preprocessing conditions, reconstruction conditions, and image processing conditions matching those designated by the user, the process shifts to step S14. Otherwise, the process shifts to step S15.

(Step S14)

The system control unit 18 outputs the display image data specified in step S13 to the display unit 19. The process then shifts to step S39 in FIG. 6.

(Step S15)

If the storage unit 15 stores display image data stored together with primary preprocessing conditions, secondary preprocessing conditions, and reconstruction conditions matching those designated by the user, the process shifts to step S16. Otherwise, the process shifts to step S17.

(Step S16)

The system control unit 18 outputs the display image data specified in step S15 to the image processing unit 123. The process then shifts to step S37 in FIG. 6.

(Step S17)

If the storage unit 15 stores the second projection data (projection data) stored together with primary preprocessing condition and secondary preprocessing conditions matching those designated by the user, the process shifts to step S18. Otherwise, the process shifts to step S19.

(Step S18)

The system control unit 18 outputs the second projection data (projection data) specified in step S17 to the reconstruction unit 122. The process then shifts to step S35 in FIG. 6.

(Step S19)

If the storage unit 15 stores the first projection data stored together with primary preprocessing conditions matching those designated by the user, the process shifts to step S20. Otherwise, the process shifts to step S21.

(Step S20)

The system control unit 18 outputs the first projection data specified in step S19 to the secondary preprocessing unit 1212. The process then shifts to step S33 in FIG. 6.

(Step S21)

The system control unit 18 outputs pure raw data to the primary preprocessing unit 1211. The process then shifts to step S31 in FIG. 6.

(Write Function)

The write function is a function of making the system control unit 18 of this X-ray computed tomography apparatus store at least one of intermediate image data and final image data in the storage unit 15, together with CT reconstruction conditions in accordance with storage conditions. Processing associated with the write function (to be referred to as write processing hereinafter) is executed together with CT reconstruction processing. Write processing will be described, together with CT reconstruction processing, with reference to FIG. 6.

FIG. 6 is a flowchart concerning CT reconstruction processing including write processing by the X-ray computed tomography apparatus according to this embodiment. Assume that the first projection data, the second projection data, image data, and display image data are designated as storage conditions by the user.

(Step S31)

The primary preprocessing unit 1211 generates the first projection data by executing primary preprocessing for pure raw data under primary preprocessing conditions designated by the user.

(Step S32)

The system control unit 18 stores the first projection data generated in step S31, together with the primary preprocessing conditions, in the storage unit 15.

(Step S33)

The secondary preprocessing unit 1212 generates the second projection data by executing secondary preprocessing for the first projection data under secondary preprocessing conditions designated by the user.

(Step S34)

The system control unit 18 stores the second projection data generated in step S33 in the storage unit 15 together with the primary preprocessing conditions and the secondary preprocessing conditions.

(Step S35)

The reconstruction unit 122 generates image data by executing reconstruction processing for the second projection data under reconstruction conditions designated by the user.

(Step S36)

The system control unit 18 stores the image data generated in step S35 in the storage unit 15 together with the primary preprocessing conditions, the secondary preprocessing condition, and the reconstruction conditions.

(Step S37)

The image processing unit 123 generates display image data by executing image processing for image data under image processing designated by the user.

(Step S38)

The system control unit 18 stores the display image data generated in step S37 in the storage unit 15 together with the primary preprocessing conditions, the secondary preprocessing conditions, the reconstruction conditions, and the image processing conditions.

(Step S39)

The display image data generated in step S37 is displayed on the display unit 19.

An example of a CT reconstruction processing setting screen provided by the CT reconstruction processing setting support unit 13 of the X-ray computed tomography apparatus according to this embodiment will be described below with reference to FIGS. 7 and 8.

FIG. 7 shows the first example of a CT reconstruction processing setting screen provided by the CT reconstruction processing setting support unit 13 of the X-ray computed tomography apparatus according to this embodiment. Assume that the second projection data, image data, and display image data are designated as storage conditions.

FIG. 7A is a view showing a change in the display form of part of a CT reconstruction processing setting screen as the first example in accordance with the first example of CT reconstruction conditions selected by the user.

FIG. 7B is a view showing a change in the display form of part of the CT reconstruction processing setting screen as the first example in accordance with the second example of CT reconstruction conditions selected by the user.

As shown in FIGS. 7A and 7B, a CT reconstruction processing setting screen 50*a* displays a CT reconstruction processing data use notification field 501, a processing item field 502, a preprocessing condition field 503, a reconstruction condition field 504, an image processing condition field 505, and a processing start button 506. A plurality of notations are arranged in the CT reconstruction processing data use notification field 501 in accordance with a processing sequence. As shown in FIG. 7A, a plurality of notations are represented by graphic patterns. A plurality of processing names are displayed in the form of a list in the processing item field 502. In this case, the plurality of processing names are arranged in correspondence with a plurality of graphic patterns. Of the plurality of graphic patterns, therefore, graphic patterns 501*a*, 501*b*, and 501*c* respectively correspond to preprocessing, reconstruction processing, and image processing. A plurality of processing condition fields are arranged in correspondence with the plurality of processing names. For example, the preprocessing condition field 503 is arranged below the processing name "secondary preprocessing". The reconstruction condition field 504 is arranged below "reconstruction processing". The image processing condition field 505 is arranged below "image processing". The preprocessing condition field 503, the reconstruction condition field 504, and the image processing condition field 505 respectively include a plurality of preprocessing conditions, a plurality of reconstruction conditions, and a plurality of image processing conditions. These CT reconstruction conditions are arranged together with check boxes, respectively. The processing start button 506 is a button for triggering this X-ray computed tomography apparatus to perform CT reconstruction processing in accordance with CT reconstruction conditions designated by the user.

The display unit 19 displays a check box corresponding to a CT reconstruction condition designated by the user distinctly from the remaining check boxes. More specifically, the display unit 19 changes the display form of the check box corresponding to the CT reconstruction condition designated by the user. For example, as shown in FIG. 7A, the display unit 19 changes and displays the color of a check box 503*a* corresponding to the CT reconstruction condition designated by the user, thereby discriminating the check box 503*a* from other check boxes (e.g., a check box 503*b*).

The display unit 19 changes the display form of each of a plurality of graphic patterns displayed in the CT reconstruction processing data use notification field 501 in accordance with an output from the system control unit 18. The display unit 19 changes the display form of each of a plurality of graphic patterns in accordance with a designated CT reconstruction condition.

The system control unit 18 searches the storage unit 15 in accordance with designated secondary processing conditions, designated reconstruction conditions, and designated image processing conditions. Assume that the storage unit 15 stores image data accompanied by secondary preprocessing conditions and reconstruction conditions matching those designated. In this case, in order to display the graphic patterns 501*a* and 501*b* distinctly from the other graphic pattern (the graphic pattern 501*c*) under the control of the system control unit 18, for example, the display unit 19 changes and displays the color of the graphic patterns 501*a* and 501*b*, as shown in FIG. 7A. The CT reconstruction processing data use notification field 501 indicates that the storage unit 15 stores image data together with secondary preprocessing conditions and reconstruction conditions matching those designated by the user. This allows the user to check the presence/absence of intermediate image data which can be used under designated CT reconstruction conditions by seeing a change in the display form of each graphic pattern. That is, since each graphic pattern aims at notifying the presence/absence of intermediate image data corresponding to a specific processing sequence, it is possible to use other notations, e.g., text information. This X-ray computed tomography apparatus can notify the user that he/she can use intermediate image data having undergone processing which has progressed to preprocessing and reconstruction processing of designated CT reconstruction conditions.

Assume that the storage unit 15 stores image data accompanied by secondary preprocessing conditions matching those designated. In this case, in order to display the graphic pattern 501a distinctly from the other graphic patterns (the graphic patterns 501b and 501c) under the control of the system control unit 18, for example, the display unit 19 changes and displays the color of the graphic pattern 501a, as shown in FIG. 7B. The CT reconstruction processing data use notification field 501 indicates that the storage unit 15 stores the second projection data together with secondary preprocessing conditions matching those designated by the user. With this operation, this X-ray computed tomography apparatus can notify the user that he/she can use intermediate image data having undergone processing which has progressed to preprocessing of designated CT reconstruction conditions. The above can be summarized as follows. The CT reconstruction processing setting screen as the first example shown in FIG. 7 enables this X-ray computed tomography apparatus to notify the user of the presence/absence of intermediate image data which can be used under CT reconstruction conditions designated by the user.

FIG. 8 shows the second example of a CT reconstruction processing setting screen provided by the CT reconstruction processing setting support unit 13 of the X-ray computed tomography apparatus according to this embodiment. Assume that the second projection data, the image data, and the display image data are designated as storage conditions.

FIG. 8A is a view showing a change in the display form of part of a CT reconstruction processing setting screen as the second example in accordance with the first example of CT reconstruction conditions selected by the user.

Figure 8B:
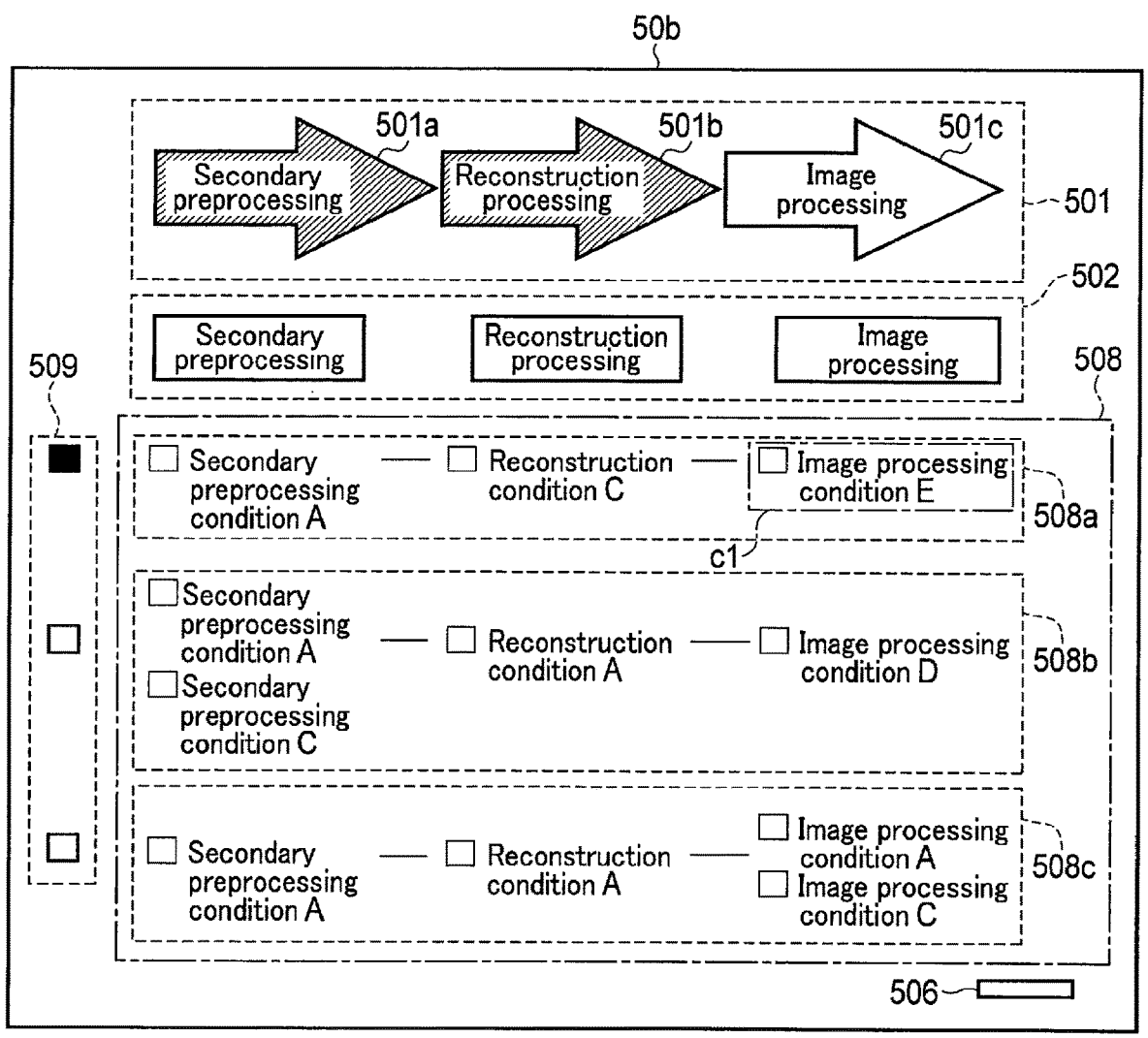
FIG. 8B is a view showing a change in the display form of part of the CT reconstruction processing setting screen as the second example in accordance with the second example of CT reconstruction conditions selected by the user.

FIG. 8B is a view showing a change in the display form of part of the CT reconstruction processing setting screen as the second example in accordance with the second example of CT reconstruction conditions selected by the user.

As shown in FIGS. 8A and 8B, the CT reconstruction processing data use notification field 501, the processing item field 502, the processing start button 506, a CT reconstruction condition field 508, and a selection field 509 are displayed on a CT reconstruction processing setting screen 50b. A plurality of CT reconstruction condition fields are arranged in the CT reconstruction condition field 508. The plurality of CT reconstruction condition fields correspond to a plurality of CT reconstruction condition sets. A CT reconstruction condition set is that executed in the past. Therefore, for example, in each of a plurality of CT reconstruction condition fields, CT reconstruction conditions executed in the past are arranged in accordance with a processing procedure.

For example, with a first CT reconstruction condition field 508a in FIG. 8A, this X-ray computed tomography apparatus can notify the user of the following matters. That is, this indicates that the storage unit 15 stores the second projection data obtained by executing secondary preprocessing for the first projection data based on secondary preprocessing condition A. In addition, this indicates that the storage unit 15 stores image data obtained by executing reconstruction processing for the second projection data based on reconstruction condition C. Furthermore, this indicates that the storage unit 15 stores display image data obtained by executing image processing for the image data based on image processing condition B. A plurality of processing conditions included in each reconstruction processing condition field are arranged together with check boxes.

A plurality of check boxes are arranged in the selection field 509. The plurality of check boxes respectively correspond to a plurality of CT reconstruction condition fields. For example, a check box 509a corresponds to the first CT reconstruction condition field 508a. The check boxes in the selection field 509 allow the user to select CT reconstruction conditions, of a plurality of CT reconstruction conditions executed in the past, which are to be used.

When the user designates the check box 509a, the display unit 19 changes the display form of the check box 509a to display the check box 509a distinctly from the remaining check boxes (check boxes 509b and 509c). It is also possible to change the display form of a plurality of check boxes in the first CT reconstruction condition field 508a corresponding to the check box 509a. For example, as shown in FIG. 8A, the display unit 19 changes the color of the check box 509a designated by the user to discriminate the check box 509a from the remaining check boxes (e.g., the check box 509b). This allows the user to designate preprocessing condition A, reconstruction condition C, and image processing condition B as CT reconstruction conditions. Since these CT reconstruction conditions are conditions executed in the past, the storage unit 15 stores display image data together with a secondary preprocessing condition, a reconstruction condition, and an image processing condition matching secondary preprocessing condition A, reconstruction condition C, and image processing condition B. For this reason, the display unit 19 notifies the user that display image data which can be used is stored in the storage unit 15. That is, the display unit 19 changes the display form of each of a plurality of graphic patterns displayed in the CT reconstruction processing data use notification field 501. Referring to FIG. 8A, the display unit 19 displays the graphic patterns 501a, 501b, and 501c upon changing their colors. This enables this X-ray computed tomography apparatus to notify the user that he/she can use display image data having undergone the progression of processing to preprocessing, reconstruction processing, and image processing of designated CT reconstruction conditions.

In addition, for example, referring to FIG. 8A, assume that the check box 509a has been designated, and image processing condition B of the CT reconstruction condition sets included in the first CT reconstruction condition field 508a has been changed to image processing condition E. In this case, the system control unit 18 searches the storage unit 15 for display image data stored together with a secondary preprocessing condition, a reconstruction condition, and an image processing condition respectively matching secondary preprocessing condition A, reconstruction condition C, and image processing condition E. Assume that the search result indicates that the storage unit 15 stores no display image data stored together with a secondary preprocessing condition, a reconstruction condition, and an image processing condition matching preprocessing condition A, reconstruction condition C, and image processing condition E. In this case, the display unit 19 displays the graphic patterns 501a and 501b distinctly from the remaining graphic pattern (graphic pattern 501c). More specifically, as shown in FIG. 8B, the display unit 19 displays the graphic patterns 501a and 501b upon changing their colors. This notifies the user that there is no display image data stored together with a secondary preprocessing condition, a reconstruction CT condition, and an image processing condition matching those designated by the user, and there is image data stored together with a secondary preprocessing condition and a reconstruction condition matching those designated by the user.

The above can be summarized as follows. With the CT reconstruction processing setting screen as the second example shown in FIG. 8, this X-ray computed tomography apparatus can display CT reconstruction condition sets corresponding to CT reconstruction processing executed in the past on the CT reconstruction processing setting screen upon arranging the sets in accordance with a processing procedure. This allows the user to check CT reconstruction conditions corresponding to intermediate image data which can be used. That is, the CT reconstruction processing setting screen as the first example shown in FIG. 7 can notify the user of the presence/absence of intermediate image data which can be used only when the user designates a CT reconstruction condition. In contrast to this, the CT reconstruction processing setting screen as the second example shown in FIG. 8 can display CT reconstruction conditions respectively corresponding to intermediate image data and final image data stored in the storage unit 15 upon arranging the conditions in accordance with a processing procedure. This allows the user to efficiently use intermediate image data and final image data.

(Modification)

A modification of this X-ray computed tomography apparatus, in which this embodiment is applied to editing operation for an expert plan, will be described. In this case, an expert plan is constituted by a plurality of types of conditions concerning a series of operations including imaging, CT reconstruction processing, and image display, which are respectively suitable for examination regions and purposes. An expert plan can be edited and set in advance via the input unit 14. The storage unit 15 stores the data of a plurality of expert plans. An expert plan to be used by the user is selected via the input unit 14. Imaging, CT reconstruction processing, and image display are automatically performed in accordance with an expert plan selected via the input unit 14. The following description will exemplify a case in which a CT reconstruction condition, of an expert plane, which corresponds to acquired pure raw data is edited.

FIG. 9 shows an example of an expert plan editing screen of the X-ray computed tomography apparatus according to a modification. The CT reconstruction processing setting support unit 13 provides the expert plan editing screen. Assume that the second projection data, image data, and display image data are designated as storage conditions. Assume that referring to FIG. 9, two expert plans are edited on the expert plan editing screen.

Figure 9A:
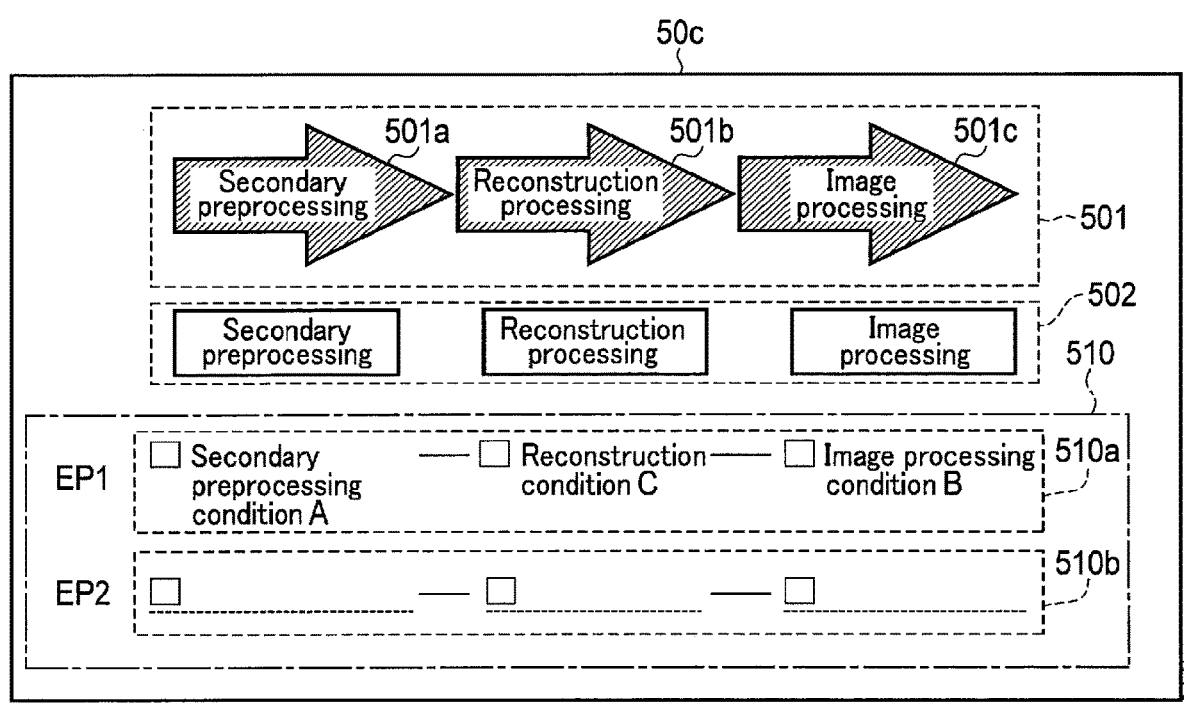
FIG. 9A is a view showing a change in the display form of part of an expert plan editing screen in accordance with the first example of CT reconstruction conditions input by the user.
Figure 10:
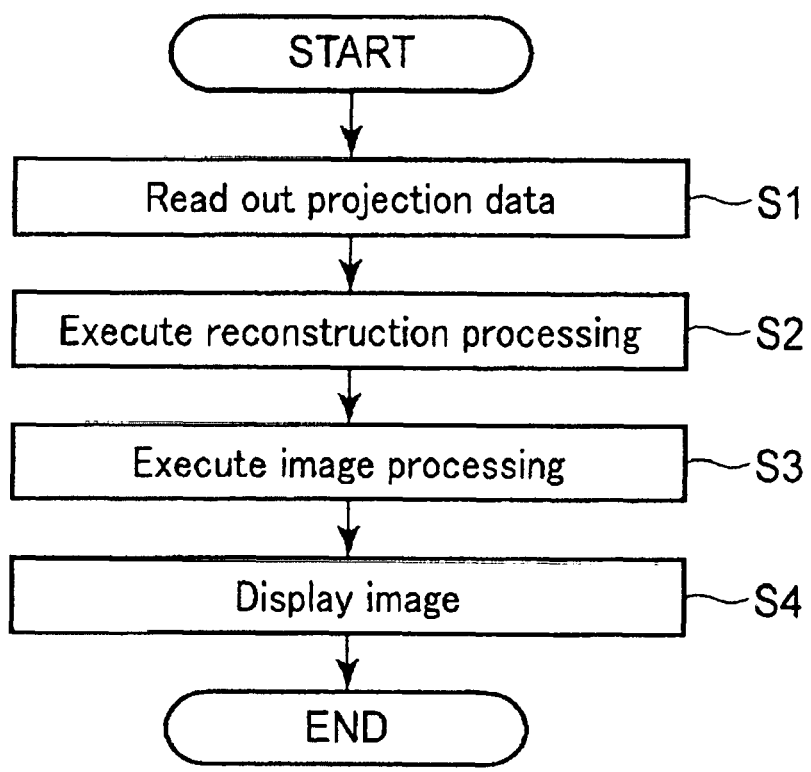
FIG. 10 is a flowchart concerning conventional CT reconstruction processing.

FIG. 9A is a view showing a change in the display form of part of the expert plan editing screen in accordance with the first example of CT reconstruction conditions selected by the user.

FIG. 9B is a view showing a change in the display form of part of the expert plan editing screen in accordance with the second example of CT reconstruction conditions selected by the user.

As shown in FIGS. 9A and 9B, the CT reconstruction processing data use notification field 501, the processing item field 502, and an expert plan field 510 are displayed on an expert plan editing screen 50c. A first expert plan field 510a and a second expert plan field 510b are arranged in the expert plan field 510. The user sets expert plans in the first expert plan field 510a and the second expert plan field 510b.

Assume that referring to FIG. 9A, a first expert plan EP1 is being edited. Assume that the user has input secondary preprocessing condition A, reconstruction condition C, and image processing condition B as CT reconstruction conditions of the first expert plan EP1 via the input unit 14. In this case, the system control unit 18 searches for a plurality of expert plans stored in the storage unit 15 in accordance with the input CT reconstruction conditions. If the search result indicates the presence of an expert plan with a secondary preprocessing condition, a reconstruction condition, and an image processing condition being set, which respectively match secondary preprocessing condition A, reconstruction condition C, and image processing condition B of the CT reconstruction conditions of the first expert plan EP1, the display unit 19 notifies the user that the input CT reconstruction conditions have already been set as an expert plan, as shown in FIG. 9A. That is, the display unit 19 changes the display form of each of a plurality of graphic patterns displayed in the CT reconstruction processing data use notification field 501. In the case shown in FIG. 9A, the display unit 19 displays the graphic patterns 501a, 501b, and 501c upon changing their colors. With this operation, this X-ray computed tomography apparatus can notify the user that processing conditions, of the designated CT reconstruction conditions, which correspond to preprocessing processing, reconstruction processing, and image processing are set in the same expert plan.

Assume that referring to FIG. 9B, a second expert plan EP2 is being edited. Assume that the user has input secondary preprocessing condition A, reconstruction condition C, and image processing condition D as CT reconstruction conditions of the second expert plan EP2 via the input unit 14. In this case, the system control unit 18 searches for a plurality of expert plans stored in the storage unit 15 in accordance with the input CT reconstruction conditions. If the search result indicates the presence of an expert plan with a secondary preprocessing condition and a reconstruction condition being set, which respectively match secondary preprocessing condition A and reconstruction condition C of the CT reconstruction conditions of the second expert plan EP2, the display unit 19 notifies the user that an expert plan having conditions matching secondary preprocessing condition A and reconstruction condition C of the input CT reconstruction conditions is set, as shown in FIG. 9B. That is, the display unit 19 changes the display form of each of a plurality of graphic patterns displayed in the CT reconstruction processing data use notification field 501. More specifically, the display unit 19 displays the graphic patterns 501a and 501b distinctly from the remaining graphic pattern (the graphic pattern 501c). For example, as shown in FIG. 9B, the display unit 19 displays the graphic patterns 501a and 501b upon changing their colors. This indicates that image data of intermediate image data generated by the first expert plan EP1 can be used for the second expert plan EP2. In other words, when the user edits an expert plan, this X-ray computed tomography apparatus can notify the user that processing conditions, of the CT reconstruction conditions designated in the expert plan, which correspond to preprocessing processing and reconstruction processing are set in the same expert plan.

The following effects can be obtained by the X-ray computed tomography apparatus according to this embodiment described above.

The X-ray computed tomography apparatus according to this embodiment having the write function stores intermediate image data corresponding to processing designated in storage conditions input by the user, together with CT reconstruction conditions executed for pure raw data to generate the intermediate image data from the pure raw data. In addition, when final image data is designated in storage conditions input by the user, the X-ray computed tomography apparatus according to the embodiment having the write function can store final image data together with CT reconstruction conditions executed for pure raw data to generate the final image data from the pure raw data. Furthermore, when pure raw data is designated in storage conditions, the X-ray computed tomography apparatus having the write function according to the embodiment can store pure raw data acquired by the data acquisition unit 109. Therefore, the X-ray computed tomography apparatus having the write function according to this embodiment can store data concerning an object which is generated accompanying CT reconstruction processing executed in the past.

For this reason, the X-ray computed tomography apparatus having the readout function according to this embodiment can specify whether there is any intermediate image data which can be used for CT reconstruction processing performed by the user, by searching the storage unit 15 in accordance with CT reconstruction conditions designated by the user via the CT reconstruction processing setting screen. It is then possible to display a display image desired by the user by executing the remaining CT reconstruction processing for the specified intermediate image data.

This X-ray computed tomography apparatus can therefore use CT reconstruction conditions in CT reconstruction processing executed in the past and intermediate image data or final image data generated accompanying CT reconstruction processing executed in the past in CT reconstruction processing in which several processes are redundant. This enables this X-ray computed tomography apparatus to improve time efficiency in diagnosis, medical treatment, and the like.

In addition, this enables the X-ray computed tomography apparatus according to this embodiment to notify the user whether intermediate image data can be used in CT reconstruction processing to be performed by the user. The CT reconstruction processing setting screen 50*a* shown in, for example, FIGS. 7A and 7B allows the user to check whether he/she can use intermediate image data or final image data stored in the storage unit 15 under CT reconstruction conditions designated by the user, from a change in the display form of each of a plurality of graphical patterns displayed in the CT reconstruction processing data use notification field 501 of the CT reconstruction processing setting screen 50*a*.

Furthermore, the X-ray computed tomography apparatus according to this embodiment can notify the user of CT reconstruction conditions executed in the past and corresponding to intermediate image data and final image data stored in the storage unit 15. For example, on the CT reconstruction processing setting screen 50*b* shown in FIGS. 8A and 8B, the display unit 19 can arrange and display CT reconstruction conditions corresponding to intermediate image data and final image data stored in the storage unit 15 in accordance with a processing procedure. The user can input CT reconstruction conditions to be executed by referring to displayed CT reconstruction conditions.

The above can be summarized as follows. A CT reconstruction processing setting screen provided by the X-ray computed tomography apparatus according to this embodiment allows the user to efficiently use intermediate image data. That is, this X-ray computed tomography apparatus can improve time efficiency in diagnosis, medical treatment, and the like.

In addition, the expert plan editing screen 50*c* provided by the X-ray computed tomography apparatus according to a modification of this embodiment allows the user to edit a plurality of expert plans registered in advance while checking whether he/she can use intermediate image data generated in accordance with a specific expert plan for another expert plan, based on a change in the display form of each of a plurality of graphic patterns displayed in the CT reconstruction processing data use notification field 501. This allows the user to set an expert plan which can efficiently use intermediate image data.

In other words, an expert plan editing screen allows the user to know in advance, upon generation of intermediate image data in accordance with set CT reconstruction conditions, whether he/she can use the CT reconstruction conditions in which the intermediate image has already been set. For example, if there is a possibility that intermediate image data generated in accordance with set CT reconstruction conditions can be used in CT reconstruction conditions which have already been set, the set CT reconstruction conditions can be said to be CT reconstruction conditions with high utility values. On the other hand, if intermediate image data generated in accordance with set CT reconstruction conditions cannot be used in CT reconstruction conditions which have already been set, the set CT reconstruction conditions can be said to be CT reconstruction conditions with low utility values. As described above, the user can set CT reconstruction conditions in an expert plan while grasping the utility values of set CT reconstruction conditions in advance. This allows the user to set CT reconstruction conditions in an expert plan so as to increase the utility values of set CT reconstruction conditions. That is, the X-ray computed tomography apparatus according to the modification of this embodiment can improve time efficiency in diagnosis, medical treatment, and the like.

Note that the write function and the readout function associated with the data processing unit 12 and the system control unit 18 of the X-ray computed tomography apparatus according to this embodiment may be used independently as an image processing apparatus. This image processing apparatus includes a transmission/reception unit. When executing the readout function, the transmission/reception unit receives pure raw data, intermediate image data, and final image data from an external apparatus under the control of the system control unit 18. In addition, when executing the write function, the transmission/reception unit transmits intermediate image data and display image data generated by the image processing apparatus, together with CT reconstruction condition data, to an external apparatus under the control of the system control unit 18.

More specifically, for example, the preprocessing unit 121 generates projection data by executing preprocessing for received pure raw data based on preprocessing conditions. The reconstruction unit 122 generates image data by executing reconstruction processing for the projection data based on reconstruction conditions. The image processing unit 123 generates display image data by executing image processing for the image data based on image processing conditions. The system control unit 18 causes the storage unit 15 to store projection data in correspondence with preprocessing conditions (the write function). In addition, the system control unit 18 reads out projection data from the storage unit 15 based on preprocessing conditions designated by the user via the input unit 14 (the readout function). This enables the image processing apparatus to obtain the same effects as those of the write function and the readout function of the X-ray computed tomography apparatus described in this embodiment.

Note that the image processing apparatus includes functions associated with the input unit 14, the storage unit 15, the CT reconstruction processing setting support unit 13, and the display unit 19 which have been described in this embodiment. This allows the image processing apparatus to obtain the effects of a CT reconstruction processing setting screen and an expert plan editing screen provided by the CT reconstruction processing setting support unit 13 described in this embodiment. Note that the functions associated with the input unit 14, the storage unit 15, the CT reconstruction processing setting support unit 13, and the display unit 19 may be included in an external apparatus connected to the image processing apparatus via an Internet line, LAN, or the like.

An embodiment of the present invention has been described above. However, this embodiment is presented merely as an example and is not intended to restrict the scope of the invention. This embodiment can be carried out in various other forms, and various omissions, replacements, and alterations can be made without departing from the spirit of the invention. These embodiments and their modifications are also incorporated in the scope and the spirit of the invention as well as in the invention described in the claims and their equivalents.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
an X-ray tube configured to generate X-rays;
an X-ray detector configured to detect X-rays generated from the X-ray tube and transmitted through an object;
a primary preprocessing circuitry configured to generate first projection data by executing primary preprocessing on data collected by the X-ray detector based on a primary preprocessing condition included in preprocessing conditions;
a secondary preprocessing circuitry configured to generate second projection data by executing secondary preprocessing on the first projection data based on a secondary preprocessing condition included in the preprocessing conditions;
a reconstruction processor configured to generate image data by executing reconstruction processing for the second projection data based on a reconstruction condition; and
control circuitry configured to cause a storage to store the first projection data in association with the primary preprocessing condition and the second projection data in association with the primary processing condition and the secondary processing condition, and to, after previous reconstruction processing is executed and when the first projection data and the second projection data are identified in the storage based on a designated preprocessing condition, read the second projection data, which is obtained later in a processing sequence than the first projection data, from the storage.

2. The X-ray computed tomography apparatus of claim 1, wherein the control circuitry is further configured to cause the storage to store the image data in association with the primary preprocessing condition, the secondary preprocessing condition, and the reconstruction condition, and to read out corresponding image data from the storage based on a designated preprocessing condition and a designated reconstruction condition.

3. The X-ray computed tomography apparatus of claim 1, wherein the storage stores data acquired by the X-ray detector.

4. The X-ray computed tomography apparatus of claim 1, wherein the control circuitry reads out data acquired by the X-ray detector from the storage when the storage stores neither projection data stored together with a preprocessing condition matching a preprocessing condition designated by a user nor image data stored together with a preprocessing condition and a reconstruction condition respectively matching a preprocessing condition and a reconstruction condition designated by the user.

5. The X-ray computed tomography apparatus of claim 1, further comprising:
a processor configured to provide a setting screen on which a plurality of notations are arranged in accordance with the processing sequence and a plurality of processing conditions concerning processes respectively corresponding the plurality of notations are arranged in association with the plurality of notations; and
a display configured to display the setting screen.

6. The X-ray computed tomography apparatus of claim 5, wherein the plurality of notations are respectively expressed by a plurality of corresponding graphic patterns, and
the processor changes a display form of each of a plurality of graphic patterns in accordance with a preprocessing condition and a reconstruction condition designated by a user.

7. The X-ray computed tomography apparatus of claim 5, wherein the processor changes a display form of the notation corresponding to a sequence of preprocessing in the processing sequence depending on whether the storage stores projection data stored together with a preprocessing condition matching the designated preprocessing condition.

8. The X-ray computed tomography apparatus of claim 7, wherein the processor changes a display form of the notation corresponding to a sequence of preprocessing in the processing sequence depending on whether the storage stores image data stored together with a reconstruction condition matching a designated reconstruction condition in addition to the preprocessing condition matching the designated preprocessing condition.

9. The X-ray computed tomography apparatus of claim 5, wherein the plurality of processing conditions correspond to a plurality of processing conditions associated with image data and projection data stored in the storage, and
the processor provides the setting screen on which the image data, a preprocessing condition, and a reconstruction condition are arranged in association with the image data.

10. The X-ray computed tomography apparatus of claim 1, further comprising a display configured to display a plurality of types of preprocessing conditions,
the display displaying a preprocessing condition, of the plurality of types of preprocessing conditions, which is stored together with projection data in the storage distinctly from other preprocessing conditions.

11. The X-ray computed tomography apparatus of claim 10, wherein the display displays a plurality of types of reconstruction conditions in addition to a plurality of types of preprocessing conditions, and displays a preprocessing condition and a reconstruction condition stored together with image data in the storage distinctly from other preprocessing conditions and other reconstruction conditions.

12. The X-ray computed tomography apparatus of claim 1, further comprising:
a storage configured to store data of a plurality of types of processing plans in which the primary preprocessing condition, the secondary preprocessing condition, and the reconstruction condition are set with respect to data acquired by the X-ray detector; and input circuitry configured to input a preprocessing condition and a reconstruction condition, wherein the processor is configured to change display forms of a plurality of notations based on a result of searching the plurality of types of processing plans by using the input preprocessing condition and the input reconstruction condition.

13. An image processing apparatus comprising:

a primary preprocessing circuitry configured to generate first projection data by executing primary preprocessing on data collected by an X-ray detector based on a primary preprocessing condition included in preprocessing conditions;

a secondary preprocessing circuitry configured to generate second projection data by executing secondary preprocessing on the first projection data based on a secondary preprocessing condition included in the preprocessing conditions;

a reconstruction processor configured to generate image data by executing reconstruction processing for the second projection data based on a reconstruction condition; and control circuitry configured to cause a storage to store the first projection data in association with the primary preprocessing condition and the second projection data in association with the primary processing condition and the secondary processing condition, and to, after previous reconstruction processing is executed and when the first projection data and the second projection data are identified in the storage based on a designated preprocessing condition, read the second projection data, which is obtained later in a processing sequence than the first projection data, from the storage.

* * * * *